(12) United States Patent
Miller et al.

(10) Patent No.: US 11,504,114 B2
(45) Date of Patent: Nov. 22, 2022

(54) BONE STAPLE STORAGE, INSERTER, AND METHOD FOR USE THEREWITH

(71) Applicant: Orthohelix Surgical Designs, Inc., Bloomington, MN (US)

(72) Inventors: Caitlin Miller, Strongsville, OH (US); Brian Hockett, Parma, OH (US); Ellen Pokorney, Medina, OH (US); Andrew Leither, Akron, OH (US)

(73) Assignee: Orthohelix Surgical Designs, Inc., Bloomington, MN (US)

( * ) Notice: Subject to any disclaimer, the term of this patent is extended or adjusted under 35 U.S.C. 154(b) by 405 days.

(21) Appl. No.: 16/703,102

(22) Filed: Dec. 4, 2019

(65) Prior Publication Data

US 2020/0100785 A1    Apr. 2, 2020

Related U.S. Application Data

(63) Continuation of application No. 15/298,873, filed on Oct. 20, 2016, now Pat. No. 10,507,021, which is a continuation of application No. 13/839,022, filed on Mar. 15, 2013, now Pat. No. 9,486,212.

(51) Int. Cl.
| | |
|---|---|
| *A61B 17/064* | (2006.01) |
| *A61B 17/068* | (2006.01) |
| *A61B 17/00* | (2006.01) |
| *A61B 17/17* | (2006.01) |
| *A61B 17/88* | (2006.01) |

(52) U.S. Cl.
CPC ...... *A61B 17/0642* (2013.01); *A61B 17/0644* (2013.01); *A61B 17/0682* (2013.01); *A61B 17/0684* (2013.01); *A61B 17/17* (2013.01); *A61B 17/8897* (2013.01); *A61B 2017/00862* (2013.01); *A61B 2017/00867* (2013.01); *A61B 2017/0645* (2013.01); *A61B 2017/0688* (2013.01)

(58) Field of Classification Search
CPC .............. A61B 17/068; A61B 17/0682; A61B 17/0684; A61B 17/0686; A61B 17/064; A61B 17/0642; A61B 17/0644; A61B 2017/07221; A61B 2017/07257
See application file for complete search history.

(56) References Cited

U.S. PATENT DOCUMENTS

| | | | |
|---|---|---|---|
| 1,989,918 A | 2/1935 | Drypolcher | |
| 2,222,744 A * | 11/1940 | Gallien, Jr. | .............. A61D 1/00 29/280 |
| 2,439,785 A | 4/1948 | Feitl et al. | |
| 2,579,484 A * | 12/1951 | Fenton | ..................... A01B 1/02 D8/10 |

(Continued)

*Primary Examiner* — Zade Coley
(74) *Attorney, Agent, or Firm* — Duane Morris LLP

(57) ABSTRACT

The invention comprises a fusion implant system for a generally u-shaped bone staple in which the staple is provided on a storage block with the two side legs in an unsplayed position, and an inserter having two triangular shaped pivoting handles has detachable tips that engage the staple on the storage block such that when the handles are aligned one over the other in a congruent position, the tips force the side legs into a splayed configuration at 90° and a sliding block holds the handles in this position to allow the staple to removed from the storage block and tamped using the inserter handles into respective bone.

8 Claims, 4 Drawing Sheets

(56) References Cited

U.S. PATENT DOCUMENTS

| | | | |
|---|---|---|---|
| 2,678,189 A | 5/1954 | Shelton | |
| 2,792,622 A | 5/1957 | Wurzel | |
| 3,041,712 A | 7/1962 | Wurzel | |
| 3,252,643 A | 5/1966 | Strekopytov et al. | |
| 3,254,649 A * | 6/1966 | Wood | A61B 17/076 606/205 |
| 3,446,212 A | 5/1969 | Le Roy | |
| 3,692,224 A | 9/1972 | Astafiev et al. | |
| 4,109,844 A * | 8/1978 | Becht | A61B 17/0684 227/19 |
| 4,217,902 A | 8/1980 | March | |
| 5,009,661 A * | 4/1991 | Michelson | A61B 17/1608 606/205 |
| 5,044,540 A | 9/1991 | Dulebohn | |
| 5,219,354 A * | 6/1993 | Choudhury | A61B 17/128 606/174 |
| 5,312,420 A * | 5/1994 | Toso | A61B 17/076 606/205 |
| 5,509,930 A * | 4/1996 | Love | A61F 2/2415 623/900 |
| 5,908,149 A | 6/1999 | Welch | |
| 6,261,296 B1 * | 7/2001 | Aebi | A61B 17/025 606/205 |
| 6,533,155 B1 * | 3/2003 | Kubota | B65C 7/005 227/67 |
| 6,685,708 B2 | 2/2004 | Monassevitch | |
| 7,055,413 B1 | 6/2006 | Wang | |
| 7,287,682 B1 | 10/2007 | Ezzat et al. | |
| 8,137,351 B2 * | 3/2012 | Prandi | A61B 17/0682 606/75 |
| 8,141,762 B2 | 3/2012 | Bedi et al. | |
| 8,172,120 B2 | 5/2012 | Boyden et al. | |
| 8,474,677 B2 * | 7/2013 | Woodard, Jr. | A61B 17/08 227/176.1 |
| 8,820,601 B2 * | 9/2014 | Gilbertson | B23P 6/00 227/71 |
| 2004/0066049 A1 * | 4/2004 | Azrikam | E01H 1/1206 294/1.4 |
| 2005/0096660 A1 * | 5/2005 | Allen | A61B 17/0642 606/75 |
| 2005/0273108 A1 * | 12/2005 | Groiso | A61B 17/0642 606/75 |
| 2007/0129733 A1 * | 6/2007 | Will | A61B 17/0642 606/108 |
| 2007/0270906 A1 * | 11/2007 | Molz | A61B 17/0642 606/219 |
| 2010/0264678 A1 * | 10/2010 | Rolling, Jr. | A47L 23/00 294/2 |
| 2011/0220701 A1 * | 9/2011 | Gilbertson | B65C 7/00 227/67 |
| 2014/0097228 A1 * | 4/2014 | Taylor | A61B 17/80 227/181.1 |

* cited by examiner

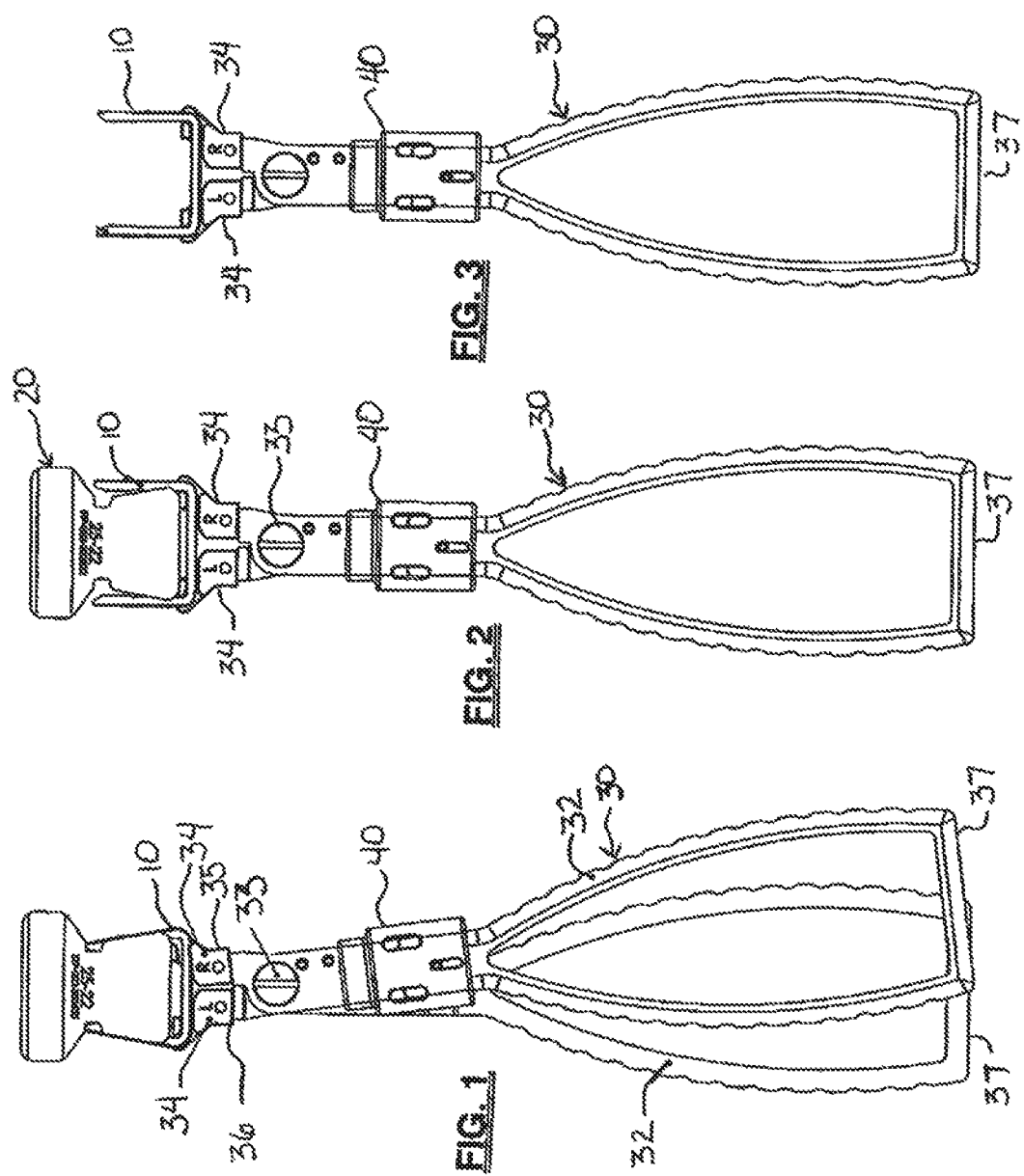

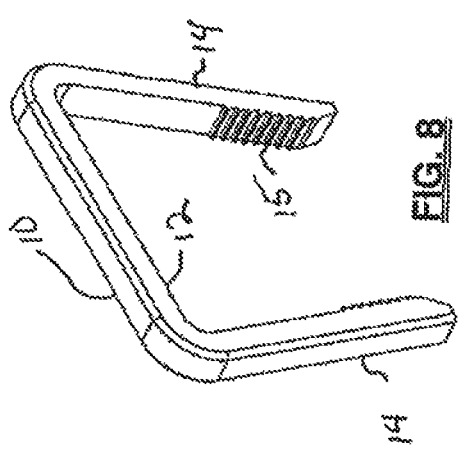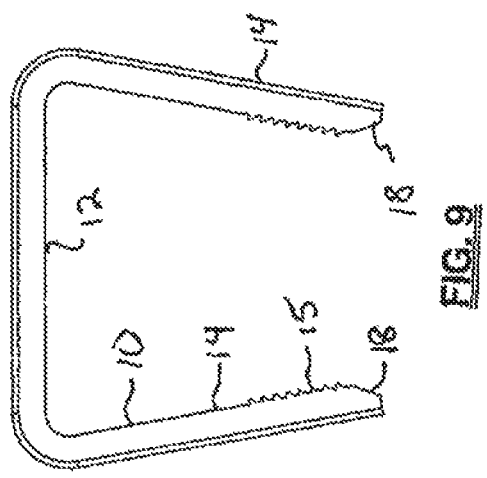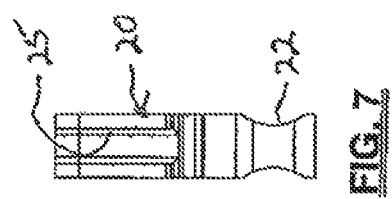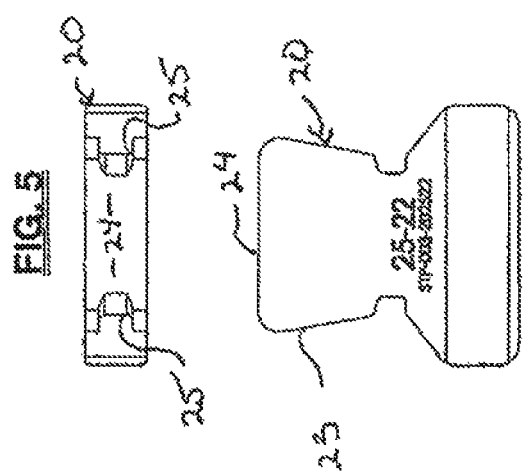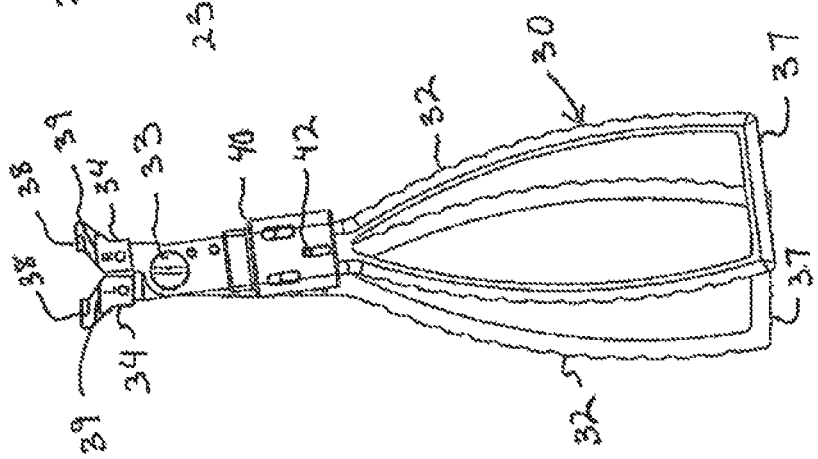

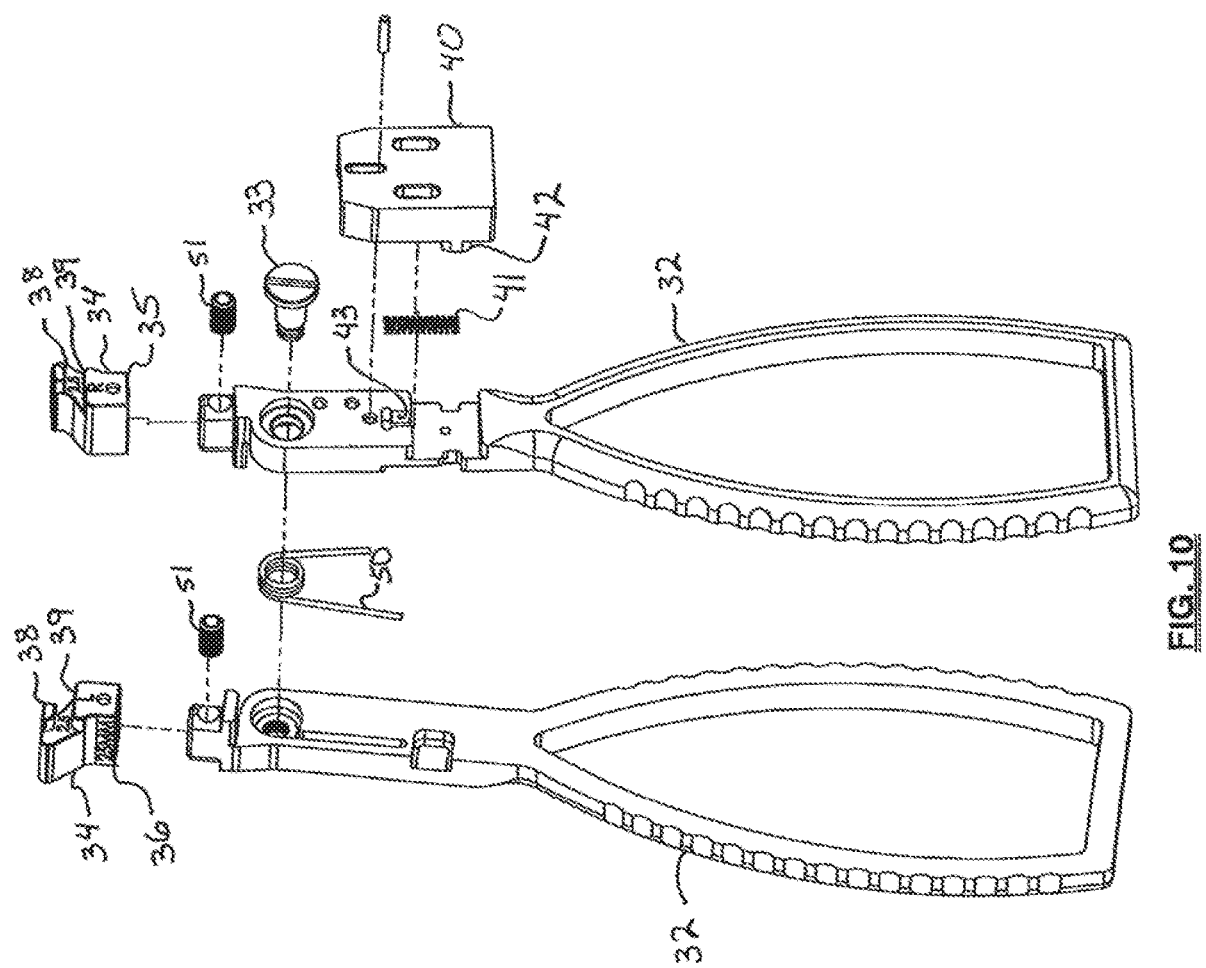

BONE STAPLE STORAGE, INSERTER, AND METHOD FOR USE THEREWITH

CROSS-REFERENCE TO RELATED APPLICATIONS

This application is a continuation of U.S. patent application Ser. No. 15/298,873, filed on Oct. 20, 2016, which is a continuation of U.S. patent application Ser. No. 13/839,022, filed on Mar. 15, 2013, now U.S. Pat. No. 9,486,212, the entireties of which are incorporated herein by reference.

FIELD OF THE INVENTION

The present disclosure relates to an invention, which involves self-compressive orthopedic bone staples which derive this characteristic from the super-elastic and/or shape memory material from which they are made. The staples have a generally U-shaped configuration comprising a central web and two extending convergent legs, optionally including barbs to hold the staple in position in bone. In accordance with the invention, the staples are provided in a surgical caddy on a storage block in an unsplayed position in which the legs each form an angle of less than 90° relative to the web member. Also provided in the surgical caddy Is a staple holder/tamp/inserter instrument which is used to dislodge the staple from the storage block by opening the staple legs to about 90° which releases the staple from the storage block and allows each of the two legs of the staple to be partially tamped into a separate bone segment while the staple is held by the inserter. Once released from the inserter, the staple subsequently causes compression between the bone segments to promote fusion between the segments.

BACKGROUND OF THE INVENTION

Despite the importance of fully functional joints for movement and balance, there are instances in which the pain that can be generated by certain pathologies justify fusion in order to alleviate on-going pain. It is sometimes necessary or desirable to cause fusion or arthrodesis of the bones that form the support structure of the lower leg or hand, for example, in the case of osteoarthritis, post-traumatic osteoarthritis, ankle arthritis or after failure of previous surgical intervention. Arthrodesis fuses the bones of the joint completely, making one continuous bone, and are used to treat conditions in the lower leg and hand, including the hind-foot, ankle, mid-foot, and phalanges.

In accordance with the prior art, fusion surgery involves debriding adjacent bone segments, aligning them as desired and using pins, plates and screws, or rods to hold the bones in the proper position while the joint(s) fuse. Sometimes, the surgeon will add natural or artificial bone graft in order to assist the fusion process, The surgeon may use graft from the patient (a piece of bone, taken from one of the lower leg bones or the wing of the pelvis) to replace the missing bone. If the alignment of the bone is improper, or if the patient is at risk or Is non-compliant and uses the joint before it is fully healed, the bones sometimes fuse into a position known as "mal-union". In more severe instances, the bones do not fully fuse which results in "non-union". There are two types of non-union; fibrous non-union, and false joint (pseudarthrosis). Fibrous nonunion refers to fractures that have healed by forming fibrous tissue rather than new bone, Pseudarthrosis refers to non-unions in which continuous movement of the fracture fragments has led to the development of a false joint.

Prior art hardware for use in arthrodesis includes wires, screws, plates and intramedullary devices. While such devices exist, each is lacking in providing one or more of the desired precision, stability, fixation, or relative ease of implantation that an orthopedic surgeon desires for such a device. Super-elastic and shape memory bone staples provide an answer to many of these issues, but a more desirable method of storage and insertion represents an improvement over the prior art.

Thus, it is an object of the present invention is to provide a bone fusion system and surgical method for implanting an implant in a mammal (including specifically humans, and domestic pets and livestock, like horses, cattle, sheep, goats, dogs, and cats), which allows for fusion of the bones or bone segments in particular of an extremity. The method includes using an incision to access the bone or bone segments to be fused, debriding and aligning the bones or bone segments, selecting a bone staple of the proper size, mounting a bone staple from a storage block on an inserter by engaging the staple with the tips of the inserter and aligning the handle of the inserter to cause the legs of the staple to splay into an open position orthogonal to the web of the staple which disengages the storage block. Further in this method, a slide inhibits the inserter legs from returning to the un-splayed position while the staple is in position on the inserter so that the staple can be tamped into the adjacent bone using the inserter to transmit the force. (Without such a provision, the legs would immediately assert a force to return to the un-splayed position such that implanting the staple becomes increasing difficult as the legs move out of the orthogonal positions.) When the staple is in position in the bone so far as possible using the inserter as a combination holder/tamp, the locking slide is repositioned so that the handles can be returned to the open position and the staple can be disengaged from the tips of the inserter. The inserter includes a section of the handles, which allow the staple legs to be implanted in the bone or bones by tamping the handles and transmitting the force to the staple to anchor it in the bone or bones. The staple can be tamped further into the bone as necessary, and the wound can be closed. In some instances a further tamp Is used to implant the staple into a position in which the staple web is as close as possible to (i.e. at or below) the bone surface.

The staple will subsequently apply a compressive force (parallel to the web member) to the adjacent bone segments to press them into contact as the staple legs act to return to an unsplayed position in which the staple legs are at an angle of less than 90° relative to the staple web or bridge.

SUMMARY OF THE INVENTION

An object of the present invention is therefore to provide a system for bone fusion which improves upon the shortcomings of the prior art and to provide novel systems and methods for immobilizing bones or bone segments to be fused in humans and in other animals such as dogs and horses.

A further object of the invention is to provide a novel instrument for storing, mounting, and inserting elastic bone staples, along with the surgical method of implanting the staples and of enabling fusion between bones or bone segments, Thus, the present invention has a goal of making it possible to perform arthrodesis under good operating conditions while also making it possible to obtain bone fusion that is particularly stable, strong, precise, and comfortable for the patient and that is particularly successful under all conditions of bone quality or pathology.

Thus, the invention provides a bone staple system including a super-elastic shape memory staple having a central web member which links two barbed legs at an un-splayed angle of less than 90° relative to the central web, and where the staple is provided during surgery on a storage block having a grip and a mounting body that securely cradles the staple in the un-splayed position, and an inserter/holder/tamp is used to dislodge the staple from the storage block as size specific inserter tips engage the staple and wherein an congruent alignment of the handles of the inserter transfers forces through the tips to the staple to open the staple legs to 90° where the staple releases the grooves of the storage block. When the inserter handles are aligned, a spring biased sliding lock slides into position to hold the handles in the aligned position. In this position the inserter holds the legs of the staple, which allows the staple to be inserted into bone by tamping the flat ends of the inserter handle. The staple is removed from the inserter by releasing the sliding lock and allowing the handles to return to the initial position, which disengages the staple from the inserter, The staple is inserted the remainder of the way as is necessary, and the wound is closed.

BRIEF DESCRIPTION OF THE DRAWINGS

FIG. 1 is a front view of a bone staple storage and insertion system of the present invention illustrating the staple on a storage block and the inserter in an initial engagement of the staple;

FIG. 2 is a front view of the bone staple storage and insertion system as shown in FIG. 1 with the insertion handles aligned to cause the bone staple legs to splay outwardly;

FIG. 3 is a front view of the bone staple and inserter of FIG. 1 with the staple removed from the storage block;

FIG. 4 Is a side view of the bone staple inserter of FIG. 1 with the handles open;

FIG. 5 is a top view of the storage block shown in FIG. 1;

FIG. 6 is a front view of the storage block shown in FIG. 1;

FIG. 7 is a side view of the storage block shown in FIG. 1;

FIG. 8 Is a top side view of the bone staple of FIG. 1;

FIG. 9 is a front view of the bone staple of FIG. 1;

FIG. 10 is an exploded view taken from a first side of the bone staple inserter of the present invention illustrating spring systems that bias the handles apart, and the lock towards a locked position.

BRIEF DESCRIPTION OF THE INVENTION

Figure 11:
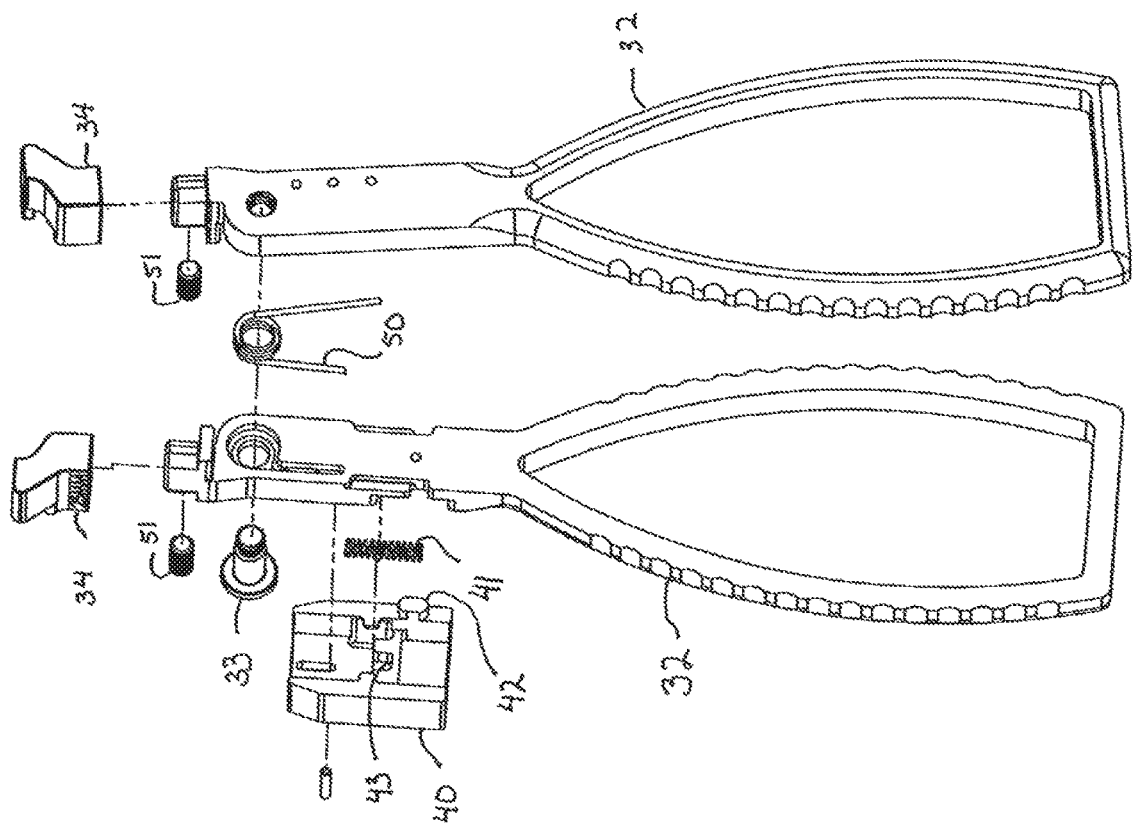
FIG. 11 is an exploded view of the bone staple inserter of FIG. 10 taken from the other side.

FIG. 1 illustrates a first embodiment of a generally U-shaped bone staple 10 made from a super-elastic and shape memory material, such as Nitinol ASTM 2063 which is super elastic between the temperatures of 0-15° C. and above (i.e, at operating room temperatures). Multiple sizes of the staple are provided ranging from 8 to 25 millimeters, Typically, the staples are provided in a variety of widths ranging in millimeter increments from 8 to 25, and varying In leg length in millimeter increments from 8 to 24 millimeters, and in corresponding thickness beginning at 1.6 millimeters and increasing to 1.9 or 2.0 or even to 2.5 millimeters for the largest size. An entire system may comprise 20 to 80 staples with multiple versions provided at each of 5 to 10 different sizes, The staple is pre-loaded in an un-splayed configuration on a storage block 20, As shown in FIGS. 8 and 9, in the un-splayed configuration, the side legs 14 of the staple 10 each form an angle of less than 90°, and preferably at an angle of from 70° to 85° more preferably at from about 75.5° to about 81°, and most preferably at from about 76.5° to about 80° relative to the base web 12 of the staple. The legs can also include a series of unidirectional barbs 15 which angle outward toward the web end of the staple help to hold the staple in position in the bone after implantation.

The storage block 20 is shown in FIGS. 5-7 from the side, front and edge respectively. The storage block includes a hand grip 22 which is integral with a storage body 23 that includes a front face 24 having two grooved areas 25 which form ramps (of from 70° to 85°, more preferably at from about 75.5° to about 81°, and most preferably at from about 76.5° to about 80° relative to the front face 24 of the body 23 or which correspond to the angle of the staple legs relative to the staple web) to capture the legs 14 of the staple at the un-splayed angle. It is preferable that the staple fits tightly on the storage block so that it is unlikely to come off without the use of the staple inserter provided with the system.

FIG. 1 further illustrates the staple 10 engaged by an inserter 30. The inserter 30 includes a pair of right and left scissoring handles 32 connected by pivot member 33 and which are in a first position (open to an angle relative to each other or from the leading edge of one handle to the opposing edge of the other handle of from about 0° or with the handles fully aligned in the splayed position, to about 7.5° or with the tips touching in the un-splayed position) in which the detachable pair of right and left tips 34 of the inserter 30 engage the inner corners formed at the junction of the inner web member 12 and the legs 14 of the staple. In this position, the staple 10 is engaged by the posts 38 on the tips in the space between the staple web or bridge 12 and the front face 24 of the storage block 20, but there is not sufficient tension of the legs 14 of the staple to cause them to open into a substantially perpendicular position relative to the web member 12. The inserter includes a spring member 50, which biases the handles into the open position, and opposes the closing force as the handles are squeezed together by a single hand. The storage block 20 includes a rounded groove 22 which forms a comfortable place for the fingers, and a necked area 28 which allows the user to see that the staple is fully seated.

When the surgeon is ready to implant the staple, he or she (or a surgical assistant) uses the inserter to engage the staple as illustrated and typically with one hand squeezes the handles 32 of the inserter 30 together to the point at which they align, and the staple can be removed from the storage block which is held in the other hand and without releasing the handles or the staple from the inserter, the staple can be mostly implanted into the bone segments (i.e. up to about 2 millimeters from the bone surface before the staple is released from the inserter).

The handles have a generally triangular shape with undulating finger grips that facilitates finding the alignment position by simply squeezing the handles inward and together. This causes the opposite ends of the inserter and the detachable inserter tips 34 to open outward and apply a pressure to the staple legs 14 so as to open them each to a substantially perpendicular position relative to the inner web 12 of the staple 10. Specifically, the inserter has a right tip 35 and a left tip 36 each of which has an inner engagement post 38 that opposes the forward surface of a web abutment member 39 on the tip across a gap that is sized to accept the width of the inner web 12 of the staple 10. In use, the web abutment members 39 hold the inner web 12 of the staple 10 in a relatively straight position while the respective inner engagement post 38 presses its respective leg outward. At the point where the staple legs 14 are about perpendicular to the staple web, a sliding lock 40 on the right handle 32 of the inserter, which is biased by a spring 41 housed in a recess 43 in the right handle and the back side of the sliding lock, toward the inserter tips simultaneously (and without the need for the user to separately manipulate the sliding lock) springs towards the pivot member or screw 33. The sliding lock 40 has a post 42 that prevents the two handles 32 from returning to their original positions with the right handle open to the right of the left handle. While the handles are open and the staple is splayed, the handles could still be pulled apart to further splay the staple. The sliding lock only prevents the inserter from returning to its original position on the respective right and left side but still allows the handles to keep splaying the staple if they are pulled apart such that the right handle Is open to the left side and the left handle is open to the right side. Thus, it is still possible, if it is medically warranted to open the legs 14 of the staple 10 past 90°.

In this "splayed" position, the staple legs 14 disengage the angled sides 22 of the storage block 20. Using the inserter 30 as a holder, the staple 10 can thus be removed from the storage block 20 in an opened position ready for deployment into bone segments. Further, when the handles 32 of the inserter align into congruence, the sliding lock member 40 slides into position and post member 42 inhibits the handles from being pressured by the legs 14 of the staple back into the first position. Each of the handles 32 include a rear section 37, and when the handles are aligned these sections can be used to tamp the staple into position in the bone by transmitting a force through the inserter to the sharp staple tips 18. To remove the inserter and tips from the staple the sliding lock is pulled away from the pivot screw and the handles will return to their original position.

As a further aspect of the invention, the staples are provided in a variety of sizes with outside web lengths ranging from 8 to 25 millimeters and outside leg lengths ranging from 8 millimeters to 24 millimeters, and accordingly, corresponding tips are provided to accommodate each of these sizes. The inserter is provided on each side with a ball detent 51 that helps to hold each respective tip in its position on the inserter. As can be seen in FIG. 10, the handles are designed to interfere past the pivot to inhibit the forces on the tips.

A surgical technique In accordance with the invention is described as follows:

Surgical Technique

Step 1: Incise the area involving the area to be fused to provide access to the bone or bone segments. Excise or debride the adjacent surfaces of the bone to be fused. Align and fix the bone using the provided k-wire.

Step 2: Using a sizer provided In the surgical caddy with the system of the present invention determine the proper size of bone staple to be used by marking the locations for the staple legs with the corresponding legs of the sizer.

Step 3: Using the sizer, mark the respective placement of the staple legs, and using the provided drill guide or k-wire, drill pilot holes for the staple legs.

Step 4: Prepare the inserter by placing the right and left tip of the proper size on the respective end of the inserter, being sure that the tip clicks into position. Using one hand engage the storage block and pre-mounted staple of the selected size, and with the other hand engage the staple web/leg interface on either side with the inserter tips. The staple web should nestle between the tip face and a tip block on either side.

Step 5: Using a single hand, squeeze the handle inwardly until they are aligned, causing the legs of the staple to splay outwardly and disengage the storage block as can be easily viewed at the necked portion of the block. With the handles aligned, the sliding lock will pop into position to hold the legs of the staple in the splayed position at 90°.

Step 6: Using the inserter to maintain the splayed position of the staple legs, position the staple legs in the pilot holes and now use the inserter as a tamp by tapping on the flat proximal ends of the handles with a mallet to transmit the force through the staple to lodge it into the bone.

Step 7: Disengage the inserter from the staple by disengaging the sliding lock and allowing the inserter handles to separate to their original position. Using the provided tamp finish implanting the staple into the bone segments as is necessary.

Step 8: Check the alignment using fluoroscopy and dose the incision.

While in accordance with the patent statutes the best mode and preferred embodiment have been set forth, the scope of the invention is not limited thereto, but rather by the scope of the attached claims.

What is claimed is:

1. A method for performing a surgery comprising:
providing a surgical caddy including a fusion implant system comprising a plurality of staples in a variety of sizes, each staple having a central web and a first leg with a first set of barbs and a second leg with a second set of barbs, a storage member which houses the staple in a position with the first and second leg at an angle of from 70° to 85° relative to the central web, and an inserter having a first handle having a first shape joined by a pivot to a second handle having a shape that is the same as the first shape, and the first handle having a first tip and the second handle having a second tip which cooperate to capture the staple wherein the first and second leg of the staple splay to a perpendicular position relative to the central web when the first handle is moved from a non-congruent alignment in which the first handle and the second handle are not overlapping to a congruent alignment over the second handle;
incising a location on a patient so as to provide access to a bone or bone segments to be fused;
excising at least one surface of the bone or bone segments and aligning the bone or bone segments prior to fixation;
determining a proper size of bone staple and marking locations on the bone or bone segments for receiving the first and second staple legs;
drilling pilot holes in the bone or bone segments for receipt of the first and second staple legs;
arranging the first and second tips of the inserter so as to engage a pre-mounted staple within the storage member with the web of the staple located between the first and second tips;
actuating the first and second handles inwardly causing the first and second staple legs to splay outwardly and disengage the storage member;
sliding a handle lock into a position to hold the first and second staple legs in the splayed position at 90°; and
positioning the first and second staple legs in the pilot holes and tapping on the first and second handles with a mallet to transmit force through the staple to lodge it into bone or bone segments.

2. The method of claim 1, further comprising disengagement of the inserter from the staple by disengaging the handle lock so as to allow the first and second handles to separate to their original position.

3. The method of claim 1, further comprising striking the first and second handles so as to implant the staple in the bone or bone segments.

4. The method of claim 1, wherein alignment of the bone or bone segments is determined by using fluoroscopy.

5. A method for performing a surgery comprising:
providing a staple system including a staple having a central web and a first leg with a first set of barbs and a second leg with a second set of barbs and the staple is stored on a storage member which houses the staple in a position with the first and second leg at an angle of from 75.5° to about 81° relative to the central web, and a staple inserter having a first handle having a first triangular shape joined by a pivot to a second handle having a second triangular shape that is the same as a first shape, and the first handle having a first detachable tip and the second handle having a second detachable tip which cooperate to capture the staple wherein the first and second leg of the staple splay to a perpendicular position relative to the central web;
incising a location on a patient so as to provide access to a bone or bone segments to be fused;
excising at least one surface of the bone or bone segments and aligning the bone or bone segments prior to fixation;
determining the proper size of bone staple and marking locations on the bone or bone segments for receiving the first and second staple legs;
drilling pilot holes in the bone or bone segments for receipt of the first and second staple legs;
arranging the inserter so as to engage a staple on the storage member;
moving the first handle from a non-congruent alignment with the second handle to a congruent alignment over the second handle;
sliding a lock on the inserter so as to spring into a position to lock the first and second handles in the congruent alignment; and
tamping the staple into adjacent bone segments by striking tamping surfaces on an end of the first triangular shaped handle and the second triangular shaped handle.

6. The method of claim 5, further comprising disengagement of the inserter from the staple by disengaging the lock so as to allow the first and second handles to separate.

7. The method of claim 5, further comprising striking the first and second handles so as to implant the staple in the bone or bone segments.

8. The method of claim 5, wherein alignment of the bone or bone segments is determined by using fluoroscopy.

* * * * *